US010622110B2

(12) United States Patent
Itu et al.

(10) Patent No.: US 10,622,110 B2
(45) Date of Patent: Apr. 14, 2020

(54) FRAMEWORK FOR PERSONALIZATION OF CORONARY FLOW COMPUTATIONS DURING REST AND HYPEREMIA

(71) Applicants: Lucian Mihai Itu, Brasov (RO); Puneet Sharma, Monmouth Junction, NJ (US); Xudong Zheng, Bangor, ME (US); Ali Kamen, Skillman, NJ (US); Constantin Suciu, Brasov (RO); Dorin Comaniciu, Princeton Junction, NJ (US)

(72) Inventors: Lucian Mihai Itu, Brasov (RO); Puneet Sharma, Monmouth Junction, NJ (US); Xudong Zheng, Bangor, ME (US); Ali Kamen, Skillman, NJ (US); Constantin Suciu, Brasov (RO); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 677 days.

(21) Appl. No.: 14/384,547

(22) PCT Filed: Mar. 13, 2013

(86) PCT No.: PCT/US2013/030732
§ 371 (c)(1),
(2) Date: Sep. 11, 2014

(87) PCT Pub. No.: WO2013/138428
PCT Pub. Date: Sep. 19, 2013

(65) Prior Publication Data
US 2015/0051888 A1 Feb. 19, 2015

Related U.S. Application Data

(60) Provisional application No. 61/611,210, filed on Mar. 15, 2012.

(51) Int. Cl.
*G16H 50/50* (2018.01)
*A61B 5/024* (2006.01)
(Continued)

(52) U.S. Cl.
CPC ............ *G16H 50/50* (2018.01); *A61B 5/021* (2013.01); *A61B 5/024* (2013.01); *A61B 5/026* (2013.01);
(Continued)

(58) Field of Classification Search
CPC ..... G06F 19/3437; A61B 6/481; A61B 5/021; A61B 5/055; A61B 5/026; A61B 5/02028;
(Continued)

(56) References Cited

U.S. PATENT DOCUMENTS

2008/0077032 A1* 3/2008 Holmes .................. A61B 5/055
600/523
2010/0241401 A1 9/2010 Martindale
(Continued)

FOREIGN PATENT DOCUMENTS

CN 100394886 8/2004
CN 1839392 9/2006
(Continued)

OTHER PUBLICATIONS

Wilson et al. "Effects of Adenosine on Human Coronary Arterial Circulation." Nov. 1990, 12 pages. (Year: 1990).*
(Continued)

*Primary Examiner* — Doon Y Chow
*Assistant Examiner* — Carina Yun (57) ABSTRACT

Embodiments relate to non-invasively determining coronary circulation parameters during a rest state and a hyperemic state for a patient. The blood flow in the coronary arteries during a hyperemic state provides a functional assessment of
(Continued)

the patient's coronary vessel tree. Imaging techniques are used to obtain an anatomical model of the patient's coronary tree. Rest boundary conditions are computed based on non-invasive measurements taken at a rest state, and estimated hyperemic boundary conditions are computed. A feedback control system performs a simulation matching the rest state utilizing a model based on the anatomical model and a plurality of controllers, each controller relating to respective output variables of the coronary tree. The model parameters are adjusted for the output variables to be in agreement with the rest state measurements, and the hyperemic boundary conditions are accordingly adjusted. The hyperemic boundary conditions are used to compute coronary flow and coronary pressure variables.

13 Claims, 8 Drawing Sheets

(51) Int. Cl.
| A61B 5/026 | (2006.01) |
| A61B 5/02 | (2006.01) |
| A61B 5/021 | (2006.01) |
| A61B 5/055 | (2006.01) |
| A61B 6/00 | (2006.01) |
| A61B 5/022 | (2006.01) |
| A61B 6/03 | (2006.01) |
| A61B 8/08 | (2006.01) |

(52) U.S. Cl.
CPC ...... *A61B 5/02007* (2013.01); *A61B 5/02028* (2013.01); *A61B 5/055* (2013.01); *A61B 6/481* (2013.01); *A61B 5/022* (2013.01); *A61B 6/032* (2013.01); *A61B 8/0891* (2013.01)

(58) Field of Classification Search
CPC ..... A61B 5/02007; A61B 5/024; A61B 6/032; A61B 8/0891; A61B 5/022
See application file for complete search history.

(56) References Cited

U.S. PATENT DOCUMENTS

| 2010/0241404 | A1* | 9/2010 | Taylor | G06F 19/3437 |
| | | | | 703/1 |
| 2011/0067697 | A1* | 3/2011 | Lellouche | A61M 16/00 |
| | | | | 128/204.23 |
| 2012/0022843 | A1* | 1/2012 | Ionasec | G06T 13/20 |
| | | | | 703/9 |
| 2012/0041318 | A1* | 2/2012 | Taylor | A61B 5/02007 |
| | | | | 600/504 |
| 2012/0053918 | A1 | 3/2012 | Taylor | |
| 2012/0059246 | A1 | 3/2012 | Taylor | |
| 2012/0072190 | A1 | 3/2012 | Chen | |

FOREIGN PATENT DOCUMENTS

| CN | 101259023 | 9/2008 |
| CN | 101290685 | 10/2008 |
| EP | 1967147 A1 | 9/2008 |

OTHER PUBLICATIONS

Huo, Yunlong, and Ghassan S. Kassab. "A hybrid one-dimensional/ Womersley model of pulsatile blood flow in the entire coronary arterial tree." American Journal of Physiology—Heart and Circulatory Physiology 292.6 (2007): H2623-H2633.
Kim, H. J. et al. "Patient-Specific Modeling of Blood Flow and Pressure in Human Coronary Arteries" Annals of Biomedical Engineering, vol. 38, No. 10, Oct. 2010, pp. 3195-3209.
Van der Horst, Arjen, et al. "A 1d wave propagation model of coronary flow in a beating heart." ASME 2011 Summer Bioengineering Conference. American Society of Mechanical Engineers, 2011.
N. Pijls and B. De Bruyne, Coronary Pressure. Springer 2000.
Itu, L., Sharma, P., Mihalef, V., Kamen, A., Suciu, C., & Comaniciu, D. (May 2012). A patient-specific reduced-order model for coronary circulation. In Biomedical Imaging (ISBI), 2012 9th IEEE International Symposium on (pp. 832-835). IEEE.
Bruinsma, P., et al. "Model of the coronary circulation based on pressure dependence of coronary resistance and compliance." Basic research in cardiology 83.5 (1988): 510-524.
Mantero, et al.; The Coronary Bed and its Role in the Cardiovascular System: A Review and an Introductory Single-Branch Model; Journal of Biomedical Engineering, vol. 14, Issue 2, Mar. 1992, pp. 109-118.
Razminia, et al; "Validation of a new formula for mean arterial pressure calculation: the new formula is superior to the standard formula." Catheterization and cardiovascular interventions 63.4 (2004): 419-425.
H. Vernon Anderson et al., "Coronary Artery Flow Velocity is Related to Lumen Area and Regional Left Ventricular Mass," Circulation, vol. 102, pp. 48-54, 2000. Circulation, vol. 102, pp. 48-54, 2000.
Zheng, Y., et al, "Four-Chamber Heart Modeling and Automatic Segmentation for 3-D Cardiac CT Volumes Using Marginal Space Learning and Steerable Features", IEEE Transactions on Medical Imaging vol. 27, No. 11, pp. 1668-1681,2008.
C. Murray, "The physiological principle of minimum work: I. The vascular system and the cost of blood volume", In Proc. of the National Academy of Sciences of the United States, vol. 12, pp. 207-214, 1926.
Kamiya, A., Togawa, T., "Adaptive Regulation of Wall Shear Stress to Flow Change in the Canine Carotid Artery", American Journal of Physiology, vol. 239, pp. 14-21, 1980.
R.F. Wilson et al., "Effects of Adenosine on Human Coronary Arterial Circulation," Circulation, pp. 1595-1606, vol. 82, No. 5, 1990.
McGinn, Andrew L., Carl W. White, and Robert F. Wilson. "Interstudy variability of coronary flow reserve. Influence of heart rate, arterial pressure, and ventricular preload." Circulation 81.4 (1990): 1319-1330.
Huo, Yunlong, et al. "A validated predictive model of coronary fractional flow reserve." Journal of the Royal Society Interface (2011).

* cited by examiner

FRAMEWORK FOR PERSONALIZATION OF CORONARY FLOW COMPUTATIONS DURING REST AND HYPEREMIA

CROSS-REFERENCE TO RELATED APPLICATIONS

This application claims priority to U.S. provisional application Ser. No. 61/611,210, filed Mar. 15, 2012, which is incorporated herein by reference in its entirety.

TECHNOLOGY FIELD

The present invention relates generally to determining coronary circulation parameters for a patient, and more particularly to a non-invasive approach utilizing a feedback control system for determining coronary circulation parameters during a rest state and a hyperemic state for a patient.

BACKGROUND

Imaging results are typically used by physicians to diagnose conditions and determine treatments related to a patient's coronary tree, such as blockages in various coronary vessels. For example, if a blockage appears to be serious, the physician may take invasive measures, such as stent insertion or surgery, to relieve the blockage. However, the imaging results alone often do not provide a complete assessment to the physician. In particular, the imaging results do not provide a functional assessment of the patient's coronary tree, which may be valuable to the physician in the diagnosis and subsequent treatment. It is thus desired to have a non-invasive approach for obtaining a functional assessment of the patient's coronary tree.

SUMMARY

Embodiments of the present invention provide for the determination of coronary circulation parameters during a rest state and a hyperemic state for a patient via non-invasive measurements and an iterative parameter estimation framework based on a feedback control system. This non-invasive approach allows for obtaining a functional assessment of the patient's coronary vessels.

According to an embodiment, determination of the coronary circulation parameters includes obtaining, via imaging, an anatomical model of a coronary tree of the patient; determining rest boundary conditions of the patient based on non-invasive measurements taken at a rest state; computing hyperemic boundary conditions of the patient; implementing a feedback control system to perform a simulation matching the rest state, wherein the feedback control system utilizes a model based on the anatomical model of the coronary tree and a plurality of controllers, each of the plurality of controllers relating to a respective output variable of the coronary tree, and wherein parameters of the model are adjusted for the output variables to be in agreement with the rest state measurements; adjusting the hyperemic boundary conditions based on the adjustments to the model; and performing a flow computation corresponding to the hyperemic state using the adjusted model.

In an embodiment, the simulation corresponding to the hyperemic state results in hyperemic output variables of the coronary tree, the hyperemic output variables comprising one or more of coronary flow and coronary pressure.

In an embodiment, the anatomical model of the coronary tree of the patient is obtained via at least one of a CT scan, an MRI scan, an angiography scan, an ultrasound scan, and a cardiac perfusion scan.

According to an embodiment, the non-invasive measurements taken at a rest state comprise one or more of heart rate, systolic blood pressure, and diastolic blood pressure.

In an embodiment, the rest boundary conditions of the patient comprise terminal resistance and capacitance values at vessel outlets during the rest state. According to an embodiment, the rest boundary conditions are adjusted using information from a cardiac perfusion exam.

In an embodiment, the hyperemic boundary conditions of the patient are a function of the rest boundary conditions of the patient and comprise terminal resistance values at vessel outlets during the hyperemic state. According to an embodiment, the hyperemic boundary conditions are adjusted using information from a cardiac perfusion exam.

In an embodiment, a first of the plurality of controllers relates to coronary resistance of the coronary tree, and a second of the plurality of controllers relates to cardiac output.

According to an embodiment, the model parameters are adjusted in a series of iterations until the output variables are in agreement with the measured patient data.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following figures.

DETAILED DESCRIPTION OF ILLUSTRATIVE EMBODIMENTS

Embodiments of the present invention relate to non-invasively determining coronary circulation parameters during a rest state and a hyperemic state for a patient. The blood flow in the coronary arteries during a hyperemic state provides a functional assessment of the patient's coronary tree, which serves as a valuable tool to a physician for diagnosis and treatment. The hyperemic state refers to a non-rest state in which the heart is pumping more blood than at the rest state. The non-invasive approach provided by embodiments of the present invention is desirable as the patient is not subjected to lengthy and/or uncomfortable invasive measures, which inherently have risks, such as, for example, infection.

According to embodiments, imaging results are used to provide an anatomical view or model of a patient's coronary vessels or coronary tree. The anatomical information provided by imaging includes such features as the size and location of blockage in the coronary tree. In order to determine how the anatomical information functionally affects the patient, embodiments of the present invention provide a method for determining the blood flow in the coronary arteries during a hyperemic state. This method is based on a novel estimation procedure for determining boundary conditions from non-invasively acquired patient data at rest. A multi-variable feedback control framework is utilized to ensure that simulated parameter values, based on the anatomical information provided by imaging, match the estimated values for an individual patient during the rest state. The boundary conditions at hyperemia are derived from the respective rest state values via a transfer function that is based on known physical characteristics and phenomena. The parameters that are the main determinants of coronary blood flow during rest state are heart rate, average aortic pressure, and the myocardial mass, for example. Since these parameters (and consequently the rest circulation) have a high variability between individuals, the main coronary diagnostic indexes are based on the hyperemic blood flow conditions, which are specific to a particular patient.

According to embodiments provided herein, the method may be summarized as follows: first the rest boundary conditions are determined, followed by a computation of the hyperemic boundary conditions. Next, a feedback control system is used to perform a simulation that matches the rest state. Finally, after establishing the hyperemic boundary conditions, the arterial model is taken out of the control loop and a simulation corresponding to the hyperemic state is performed.

Figure 1:
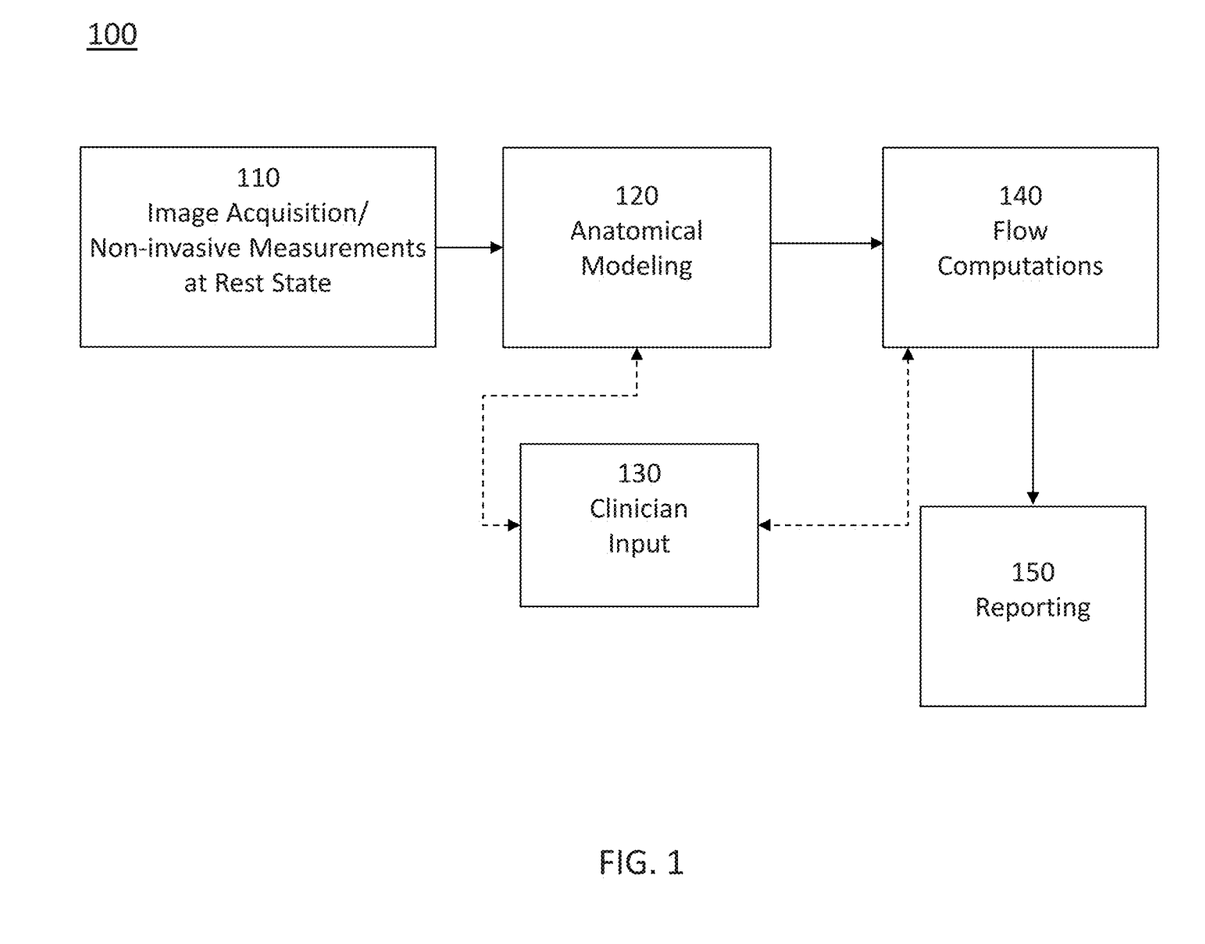
FIG. 1 is an overview representation of a workflow for non-invasively determining coronary circulation parameters during a hyperemic state for a patient, according to an embodiment.

FIG. 1 provides a high-level overview representation of the workflow 100 for non-invasively determining coronary circulation parameters during a hyperemic state for a patient. Additional aspects related to each phase of the workflow 100 are provided below in greater detail. Step 110 of the workflow 100 represents image acquisition and non-invasive measurements at a rest state of the patient. The image acquisition may be acquired with a CT scan, an MRI scan, an angiography scan, an ultrasound scan, a cardiac perfusion scan, or other technology capable of obtaining an accurate, clear image of a patient's anatomical framework. The non-invasive measurements may include, but are not limited to, heart rate and blood pressure.

At 120, anatomical modeling is performed to derive a framework based on the anatomical model of the coronary tree for the patient. The anatomical modeling may include establishing parameters with respect to the acquired image of the patient, such as, for example, flow and pressure through various portions of the coronary tree. The anatomical modeling may also include segmenting the coronary tree to focus on areas of concern for the particular patient. The anatomical modeling may involve constructing a 3D model of the patient's coronary vessels, the proximal aorta, and the myocardium.

Step 130 of the workflow 100 represents a clinician's input, including providing feedback to the anatomical model to adjust the model based on his or her knowledge or other information related to the patient, for example.

Flow computations are computed at 140, with feedback from the clinician (130 of the workflow 100) being inputted as necessary, to arrive at the functional assessment of the patient's coronary tree. The flow computations use hyperemic boundary conditions, which are adjusted as a result of applying a feedback control system that performs a simulation matching the rest state. The feedback control system utilizes a model based on the anatomical model of the coronary tree, and also includes a plurality of controllers, with each of the plurality of controllers relating to a respective output variable of the coronary tree. The model is adjusted to allow for the output variables to be in agreement with the rest state measurements. The output variables agreeing with the rest state measurements is an indication that the model accurately reflects the patient. Then, the hyperemic boundary conditions are adjusted based on the adjustments made to the model. The feedback control system is described in greater detail with respect to FIGS. 4, 5A, and 5B.

A report is provided at 150, with the report identifying results of a simulation corresponding to the hyperemic state using the adjusted model. The report includes the functional assessment of the patient's coronary tree and may include, but is not limited to, such information as fractional flow reserve (FFR) and coronary flow reserve (CFR) parameters based on the hyperemic state that serve as important diagnostic tools for a physician.

For an accurate simulation of a patient's coronary blood-flow, two key requirements for computational fluid dynamics (CFD)-based methods are (1) an anatomical model of the coronary vessel tree and (b) the boundary conditions at the inlet and outlets. Recent advances in medical image processing have addressed the former by employing manual, semi-automatic or fully-automatic algorithms for multimodality image segmentation and surface mesh generation.

Figure 2:
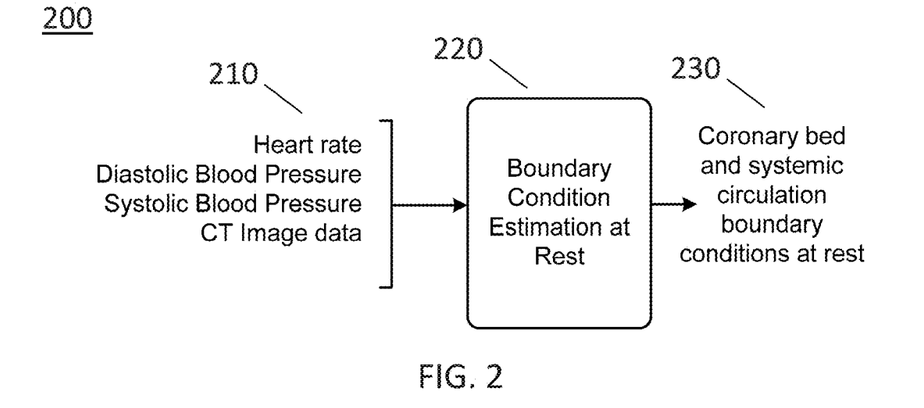
FIG. 2 is a representation of the estimation of boundary conditions at the rest state, according to an embodiment.
Figure 3:
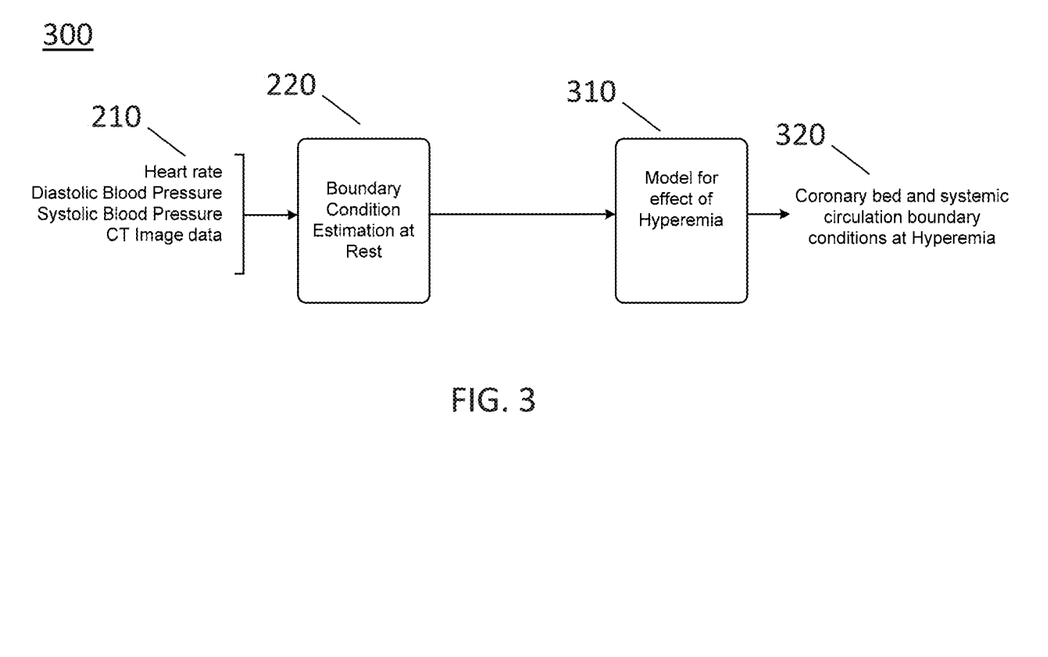
FIG. 3 is a representation of the estimation of boundary conditions at the hyperemic state, according to an embodiment.

FIG. 2 provides a representation 200 for estimating boundary conditions at the rest state, while FIG. 3 provides a representation 300 of the estimation of boundary conditions at the hyperemic state, both of which are more fully described below.

Estimation of Boundary Conditions at Rest State

Since the region of interest, namely the coronary vessel tree, is part of the larger circulation system, the inlet and outlet boundary conditions are chosen such that they adequately model the proximal and distal phenomenon of the patient's circulation. The models take into account the effect of the myocardial contraction on the flow. These lumped models are usually composed of a set of resistances and compliances, which represent the micro-vascular beds. The compliance influences the transient waveform, while the mean value is affected only by the resistance. Since the key diagnostic indexes (such as FFR and CFR) are based on average quantities over the cardiac cycle, the boundary condition estimation is limited to correctly determining the resistance values at each outlet, which is defined as the ratio of the pressure to the flow through that outlet. Mean arterial pressure (MAP) is constant in healthy epicardial arteries and can be estimated by systolic, diastolic cuff blood pressures (SBP and DBP), and the heart rate as follows:

$$MAP = DBP + [\tfrac{1}{3} + (HR \times 0.0012)](SBP - DBP).$$

Coronary flow depends on the oxygen demand of the heart, and since oxygen extraction in the coronary capillaries is close to maximum levels even at rest state, the increased metabolic need can be satisfied only through an increased flow, hence coronary flow is proportional to the oxygen demand. It is difficult to quantify oxygen demand and consumption in the coronaries through non-invasive measurements. Several methods for estimating oxygen consumption from mechanical variables have been proposed in the past, with heart rate as a primary determinant of oxygen consumption. The second major determinant is pressure (pressure generation costs more oxygen than muscle shortening, i.e. flow). The most widely used index for estimating the myocardial oxygen consumption is the rate-pressure product, according to which:

$$q_{rest} = 8 \times \{[7 \times 10^{-4}(HP \cdot SBP)] - 0.4\} \frac{ml}{min} / 100 \ g. \quad (1)$$

To determine the absolute value of resting flow ($Q_{rest}$), resting perfusion is multiplied with total myocardial mass. In normal hearts, the left ventricle typically represents two-thirds of the total mass, i.e. $Q_{rest}=q_{rest} \times 1.5 \times M_{LV}$. Hence total coronary resistance can be computed as $R_{cor}=MAP/Q_{rest}$. The value $M_{LV}$ is estimated from CT images by myocardial segmentation. The next step is to distribute the total resistance to the various lumped models at the outlets. To do this, Murray's law, which states that the energy required for blood flow and the energy needed to maintain the vasculature is assumed minimal and hence, $Q_i \sim k \ r_i^3$, where k is a constant and r is the radius of the vessel. A value of 3 for the power coefficient has been suggested through the observed invariability of wall shear stress (rate) when flow rate varies substantially. Next, the absolute resting flow, which is the sum of all outlet flows, is written as:

$$Q + rest = \Sigma_{i=1}^n k \cdot r_i^3 = \Sigma_{i=1}^n Q_i.$$

The flow through a particular outlet is determined by:

$$\frac{Q_i}{Q_{rest}} = \frac{k \cdot r_i^3}{\sum_{j=1}^n k \cdot r_j^3} \rightarrow Q_i = Q_{rest} \cdot \frac{r_i^3}{\sum_{j=1}^n r_j^3}. \quad (2)$$

Therefore, the terminal resistances can now be determined by:

$$R_i = \frac{MAP}{Q_i} = MAP \cdot \frac{\sum_{j=1}^n r_j^3}{Q_{rest} \cdot r_i^3}. \quad (3)$$

Referring to FIG. 2, the representation 200 provides a concise summary of the estimation of boundary conditions at the rest state, as described above with respect to equations (1), (2), and (3). The input parameters 210 used for the estimation include heart rate, diastolic blood pressure, systolic blood pressure, and the image data (such as CT image data). Boundary condition estimation at rest (220) is performed with the input parameters 210 and the equations (1), (2), and (3), resulting in the coronary bed and systemic circulation boundary conditions at rest (230). The boundary conditions at rest include, but are not limited to, the rate-pressure product, $q_{rest}$; the flow through a particular outlet, $Q_i$; and terminal resistances, $R_i$.

Estimation of Boundary Conditions at Hyperemia

Intracoronary and intravenously drug-induced hyperemia leads to similar decreases in micro-vascular resistances. The intravenous administration of adenosine leads to a slight increase of heart rate and decrease of blood pressure. For a simulation the effect of intracoronary vasodilator can be extended infinitely and it minimally influences the heart rate and blood pressure. Adenosine leads to an increase in coronary flow velocity of around 4.5 for normal, healthy subjects (with no coronary artery disease). Since blood pressure decreases slightly during hyperemia, a 4.5-fold increase in flow does not mean a 4.5-fold decrease in coronary resistance. A total coronary resistance index (TCRI) can be computed, which is equal to:

$$TRCI = \left(\frac{MAP_{hyper}}{Q_{hyper}} \middle/ \frac{MAP_{rest}}{Q_{rest}}\right) = \frac{(R_{cor})_{hyper}}{(R_{cor})_{rest}}. \quad (4)$$

A mean value of TCRI=0.22 has been obtained during various studies. It increases from 0.22, for HR less than 75 bpm, to 0.26, for a heart rate of 100 bpm, and to 0.28 for a heart rate of 120 bpm. Therefore, the following relationship can be derived to obtain a HR corrected TCRI:

$$TRCI_{corr} = \begin{cases} 0.0016 \cdot HR + 0.1 & \text{for } HR \leq 100 \text{ bpm;} \\ 0.001 \cdot HR + 0.16 & \text{for } HR > 100 \text{ bpm} \end{cases}.$$

Finally, hyperemic micro-vascular resistances are computed by:

$$(R_i)_{hyper} = (R_i)_{rest} \cdot TCRI \quad (5).$$

$(R_i)_{rest}$ is the value from equation (3).

Referring to FIG. 3, the representation 300 provides a concise summary of the estimation of boundary conditions at hyperemia, as described above with respect to equations (4) and (5). The input parameters 210 and the boundary condition estimation at rest state 220 are applied to a model for effect of hyperemia 310, as represented by equations (4) and (5). This results in the coronary bed and systemic circulation boundary conditions at hyperemia (320). The boundary conditions at hyperemia include, but are not limited to, total coronary resistance index, TCRI; and hyperemic micro-vascular resistances, $(R_i)_{hyper}$.

Feedback Control System

In order to accurately evaluate coronary diagnostic indexes, the goal of a CFD simulation is to obtain the same average pressure and flow rates inside the coronary arteries as that of obtained if the patient were in the rest/drug-induced intracoronary hyperemia. Since the proposed method is based on parameters acquired during the rest state, it is important to first set-up the simulation for the rest state and then make the transition to the hyperemia. The coronary resistances are determined as described above with respect to the description of the estimation of boundary conditions at rest state. As a result, if the simulated MAP matches the value determined through equation (1), the coronary flow automatically matches the estimated value. During intracoronary drug-induced hyperemia, MAP drops slightly due to the decrease in coronary resistances. To capture this aspect, the coronary tree is coupled to the aorta. This coupling also enables the use of a simplified heart model in order to provide the inlet boundary condition. If only the coronaries were modeled, then either time-varying flow or pressure would be needed at inflow, none of which is available non-invasively. Coronary flow at rest represents around 4-5% of the total cardiac output. Although the focus lies on the coronary circulation, the systemic resistances (coupled at the outlet of the aorta and of the other proximal vessels) are adapted so that the total coronary flow is around 4-5% of the cardiac output. The second reference variable is the coronary flow as a percent of the cardiac output. An accurate estimate for it during rest is important to obtain an accurate decrease in aortic pressure when performing simulation at hyperemia.

Figure 4:
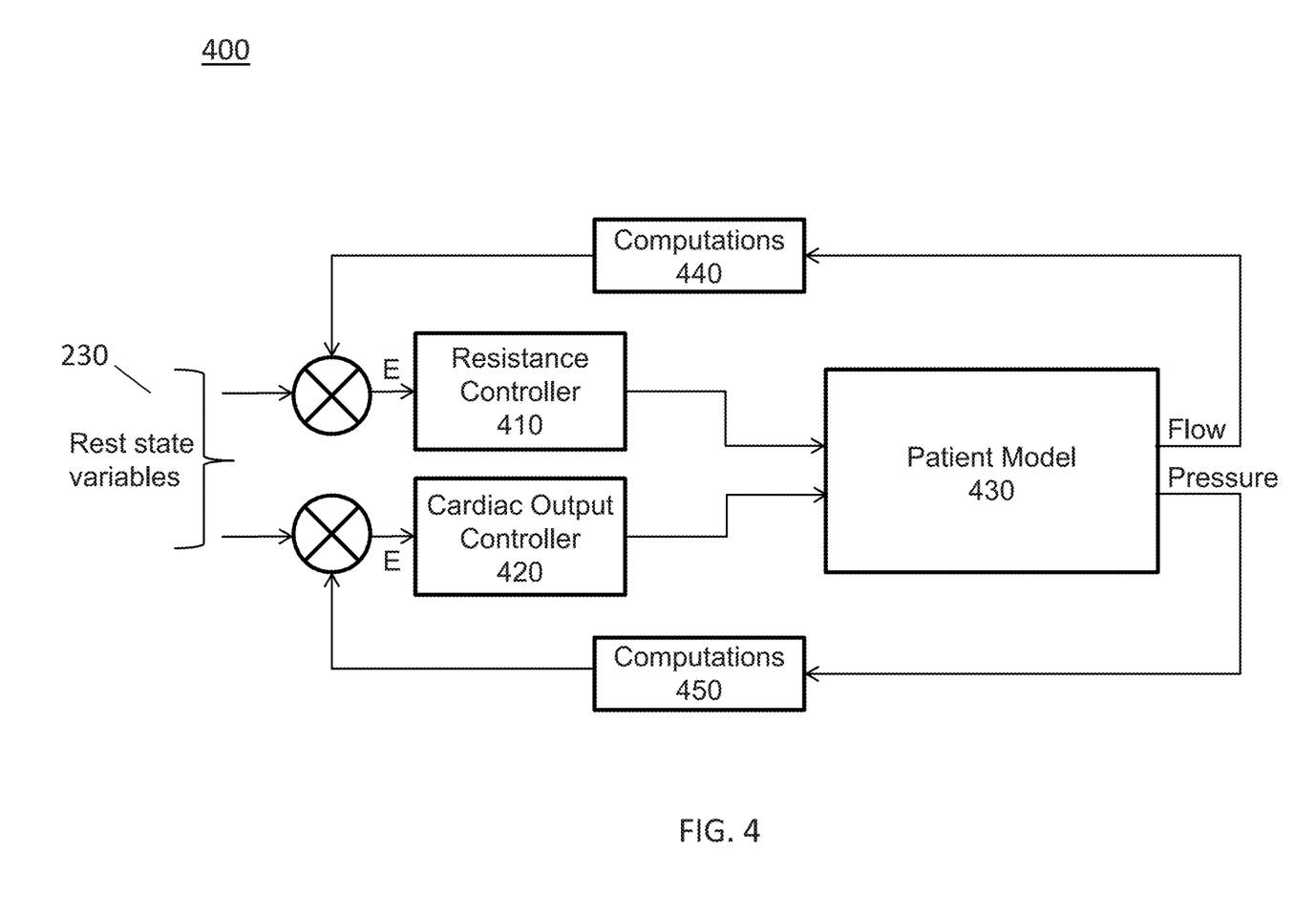
FIG. 4 is a block diagram representation of a feedback control system that is used for rest state simulation, according to an embodiment.

FIG. 4 displays the feedback control system 400 that is used for the rest state estimation and for the flow computations for the hyperemic state. The feedback control system utilizes a model 430 based on the anatomical model of the coronary tree and includes a plurality of controllers (such as controllers 410 and 420), each of which corresponds to a respective output variable of the coronary tree. As shown, the controller 410 is a systemic resistance controller relating to coronary resistance of the coronary tree, and the controller 420 is a cardiac output controller relating to the cardiac output. The systemic resistance controller is a Proportional Integral (PI) controller, while the cardiac output controller is a Proportional Integral Derivative (PID) controller. The patient model 430 (i.e., the anatomical model of the coronary tree for the patient) is used to generate simulated values of flow and pressure. The simulated values are adapted into the flow computation equations (computations 440 and 450), the results of which are compared to those derived from the non-invasive measurements. If an error (E) is determined to exist from the comparison, the controllers 410 and 420 adjust parameters of the model 430 to allow for the output variables to be in agreement with the rest state measurements. This process may take several iterations until the model 430 accurately reflects the patient. Moreover, additional controllers (not shown) may also be incorporated into the feedback control system 400. If included, each additional controller relates to another aspect of the coronary vessel tree and may increase the accuracy of the patient model 430.

Once the output variables are in agreement with the variables based on the non-invasive measurements, the hyperemic boundary conditions are accordingly adjusted based on adjustments made to the patient model 430 and are used in the flow computation equations to obtain the coronary circulation parameters (flow and pressure) during the hyperemic state for the patient.

Figure 5A:
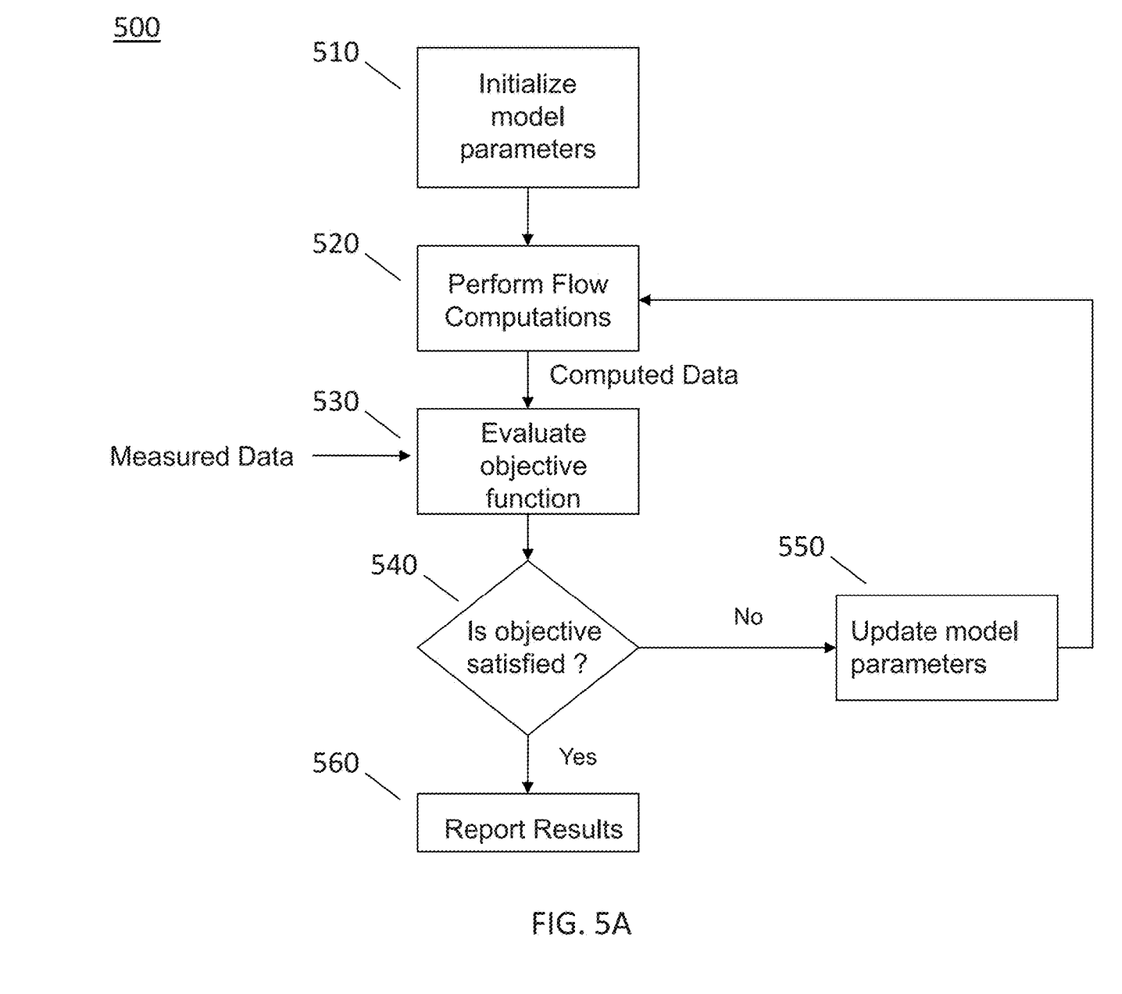
FIGS. 5A and 5B are flow charts illustrating the process of determining the coronary circulation parameters during the hyperemic state for a patient, according to an embodiment.
Figure 5B:
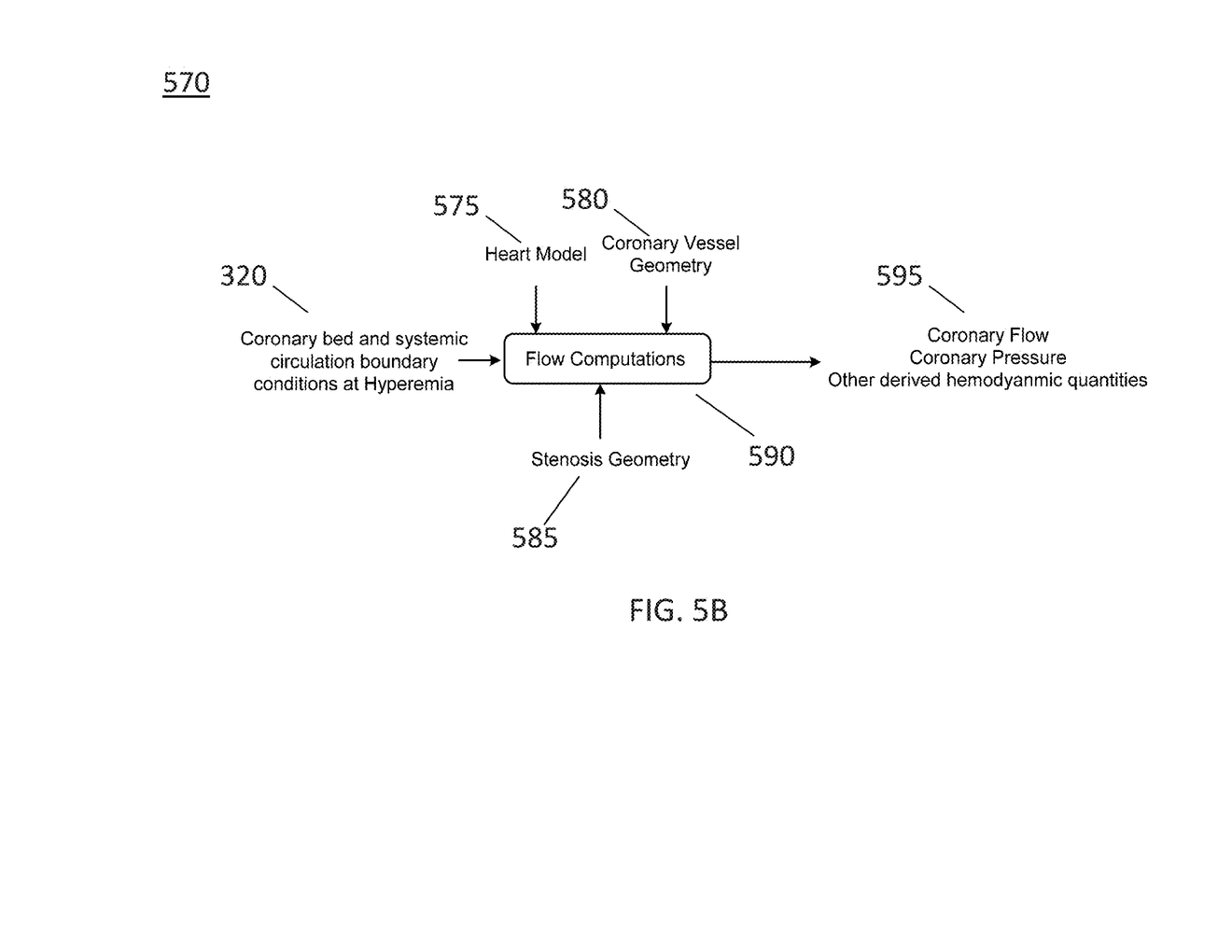

This process is further represented in the flow diagram 500 of FIG. 5A and the computation representation 570 of FIG. 5B. With reference to FIG. 5A, at 510, model parameters are initialized. This refers to the simulated values of flow and pressure, for example. At 520, flow computations are performed. At 530, a comparison is done between the measured data (based on the non-invasive measurements) and the simulated data (based on the model). At 540, a determination is made to establish if an objective is satisfied. The objective may refer to a percent error between the measured data and the simulated data. If the percent error is less than or equal to a predetermined value (which may be different for each variable), then the objective is satisfied. At 550, if the percent error is not less than the predetermined value, then the model parameters need to be updated as determined by the controllers 410 and 420. The computations at 520, the evaluation at 530, and the determination of satisfying the objective at 540 are repeated. Once the objective is satisfied, the results may be reported at 560.

FIG. 5B illustrates the computational process 570 that leads to the coronary circulation parameters (flow and pressure) during the hyperemic state for the patient. Flow computations (590), using the boundary conditions at hyperemia (320) along with a model of the heart (575) and the patient's model (580, 585), are used to derive the coronary flow and coronary pressure at hyperemia (595). These parameters may be used to determine other hyperemic variables for the patient.

From a sensitivity analysis, there are various ways to change the cardiac output of the heart model, namely the time of maximum elastance, maximum contractility, dead volume, initial left ventricle (LV) volume, systemic resistance or left atrial pressure (heart rate is given and cannot be changed). The highest sensitivity is due to the difference between initial LV volume and dead volume. Note that the goal of the proposed method is to reach a steady-state which matches the patient-specific steady-state correctly, and not necessarily model the transient aspects of the control mechanism. Once the simulation has converged and the values for the systemic resistances and for the difference between initial LV volume and dead volume have been determined, the control loop is switched off, and the rest outlet resistances are substituted by the hyperemic resistances. Thus the MAP is allowed to drop slightly and the percentage represented by the coronary flow out of the total flow becomes much higher since coronary flow increases several times. The simulation is run again until convergence.

Figure 6:
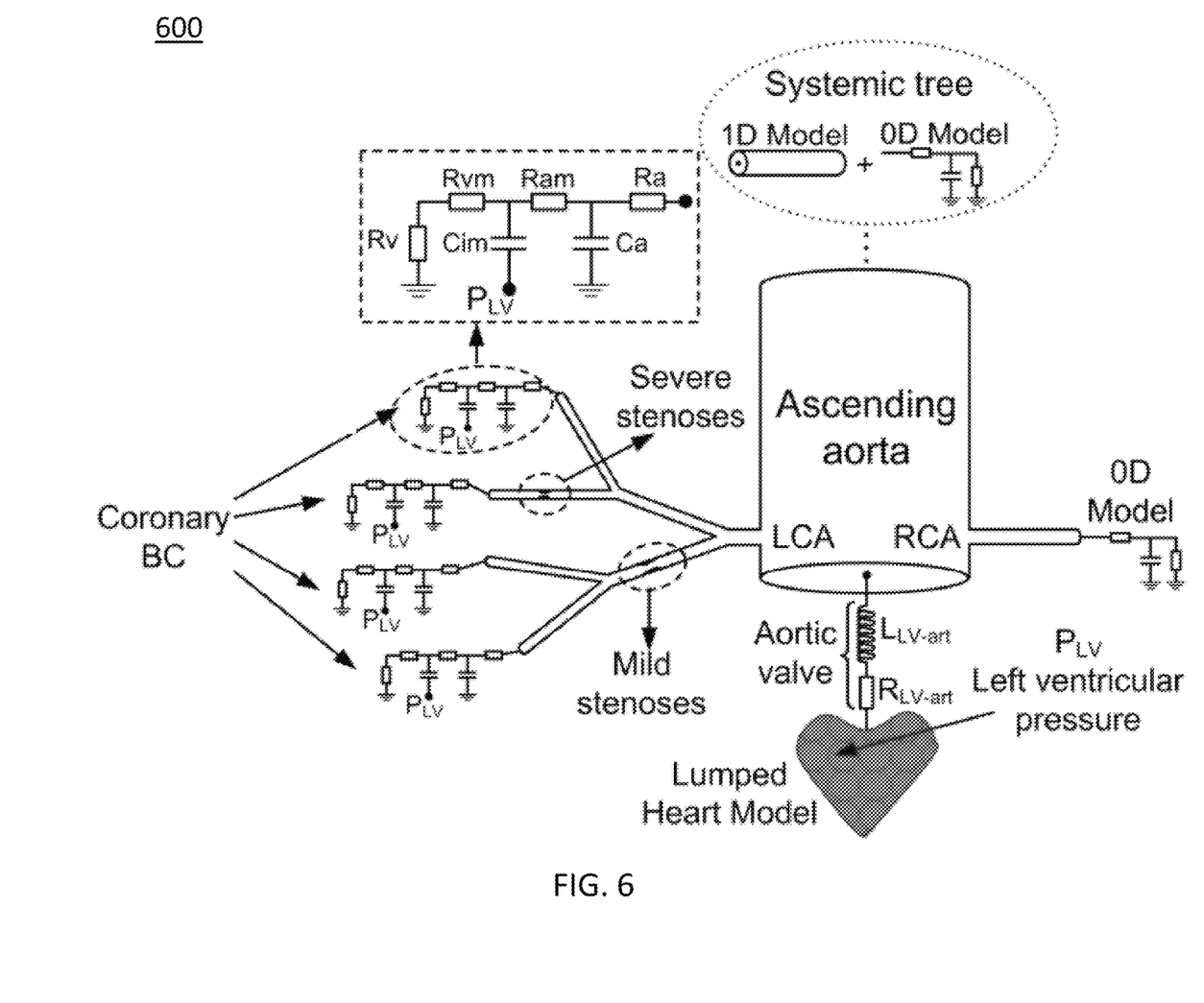
FIG. 6 is a representation of the coronary circulation system used in various embodiments.

FIG. 6 provides a representation 600 of a model of the coronary circulation, indicating the points of boundary conditions labeled as "BC". Ra indicates the proximal arterial resistance; Ca the arterial compliance; Ram microvascular arterial resistance; Cim intra-myocardial compliance (which accounts for volume reduction at systolic contraction); Rvm microvascular venous resistance; and Rv venous resistance.

The method described herein has been tested using a reduced-order patient-specific model. The proximal vessels are modeled using ID segment while the micro-vascular beds are represented either through 3-element Windkessel models, or through specialized lumped models for the coronary circulation. The total outflow resistances have been determined, while the lumped coronary models are composed of four different resistances. The first resistance is equal to the characteristic resistance in order to minimize the reflections, while the third and fourth resistances represent the micro-vascular venous and venous resistances which are considered constant. Thus the micro-vascular arterial resistance is determined as difference between the total and the three other resistances. Note that the average pressure and flow depend on total resistance and not on its distribution to the individual resistances. Patient-specific data was extracted from Coronary CTA scans by image segmentation, centerline and lumen extraction. The systemic circulation is represented by average lengths and radiuses, but this does not affect the results since the role of the systemic circulation is to correctly capture the hyperemic conditions and this goal is achieved if the rest state pressure and the percentage of coronary flow match the patient-state. An artificial 65% diameter stenosis with a length of 1.0 cm has been introduced on one of the left descending artery branches. A sensitivity analysis has been performed for the four different input parameters of the proposed method: heart rate, systolic and diastolic pressure (taken together since the MAP is the actual input), the left ventricular mass and the power coefficient n. The base values used for the analysis are: HR=60 bpm, SBP=140 mmHg, DBP=100 mmHg, LVM=250 gm, n=3. Each input parameter is varied individually by ±10%, ±20% and ±30% (except the power coefficient, where only ±10% and ±20% variations were done). The cuff pressures were varied simultaneously by the same percentage.

Figure 7A:
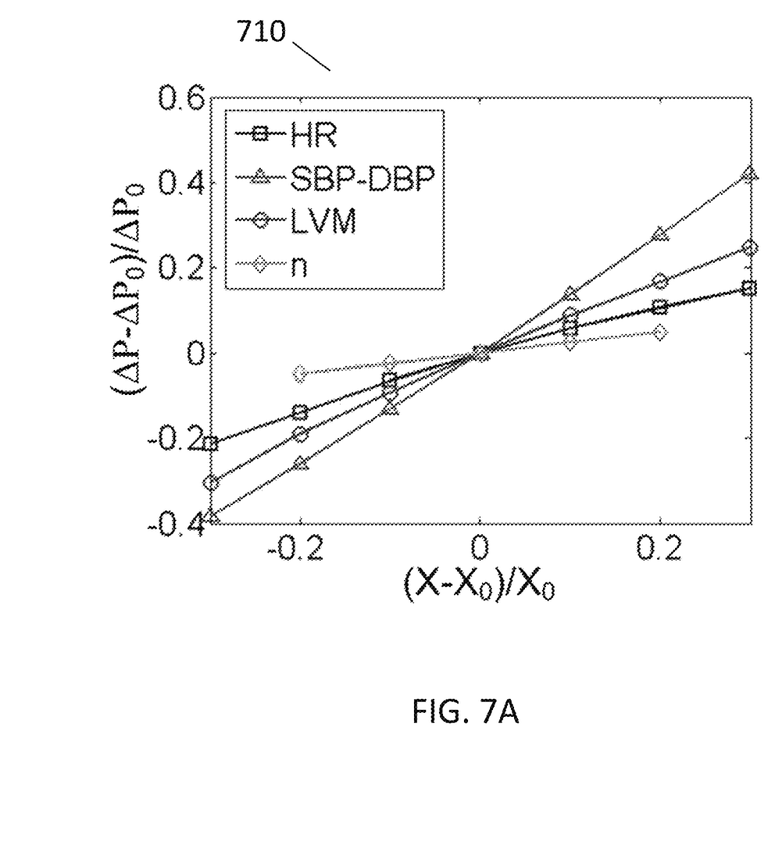
FIGS. 7A and 7B illustrate results of analyses for a test scenario of aspects of the present invention.
Figure 7B:
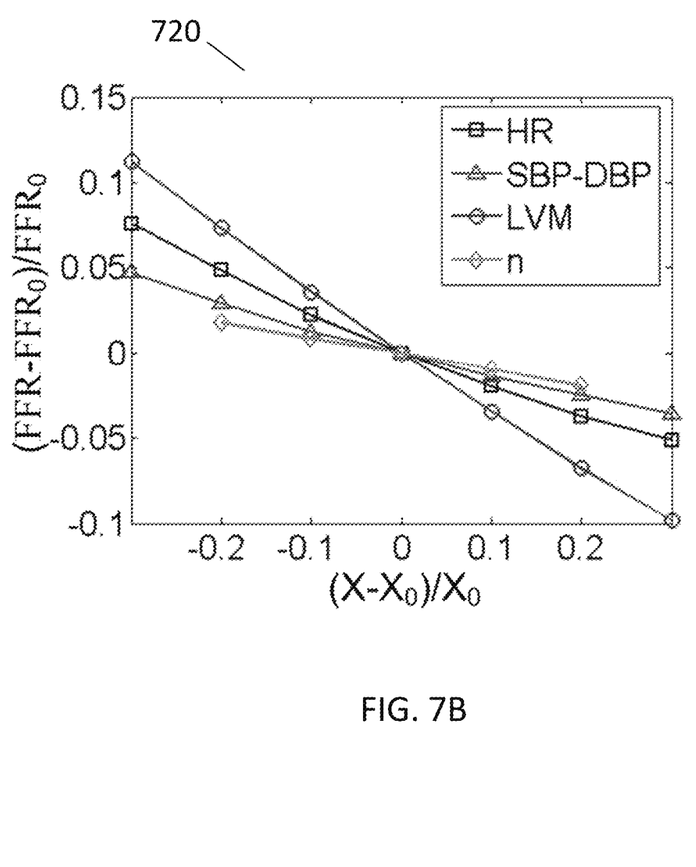

FIGS. 7A and 7B show the results, respectively 710 and 720, of the sensitivity analysis for the trans-stenotic pressure drop (P) and Pd/Pa. The highest sensitivity for P is with respect to the cuff-pressures, followed by LVM (see 710 in FIG. 7A). For FFR (Pd/Pa), the highest sensitivity is with respect to the LVM, followed by HR (see 720 in FIG. 7B). In both cases, the power coefficient has minimal influence. To further demonstrate the need for accurate outlet boundary condition estimation, the hyperemic resistances have been directly manipulated by ±10%, ±20% and ±30% and Table I below displays the results for ΔP and FFR. The results clearly show that is not sufficient to use a control loop as the one depicted in FIG. 4, or any other approach, which matches the heart rate and the pressure of the patient, but it is crucial to correctly determine the rest and hyperemic micro-vascular resistance of each outflow vessel, in order to correctly estimate the values of hemodynamic indexes. For the given case, FFR value varies between 0.628 and 0.784, an interval which intersects the cut-off value used in clinical practice.

TABLE I

| $R_{hyper}$ | $P_a$ | $P_d$ | Q | ΔP | $P_d/P_a$ |
|---|---|---|---|---|---|
| 7579 (−30%) | 100.01 | 62.79 | 2.11 | 37.22 | 0.628 |
| 8661 (−20%) | 101.64 | 67.55 | 1.99 | 34.09 | 0.664 |
| 9744 (−10%) | 102.97 | 71.67 | 1.88 | 31.30 | 0.696 |
| 10827 (0%) | 104.01 | 75.21 | 1.77 | 28.80 | 0.723 |
| 11919 (+10%) | 105.03 | 78.40 | 1.68 | 29.80 | 0.746 |
| 12993 (+20%) | 105.83 | 81.17 | 1.60 | 24.66 | 0.766 |
| 14076 (+30%) | 106.54 | 83.62 | 1.52 | 22.92 | 0.784 |

Figure 8A:
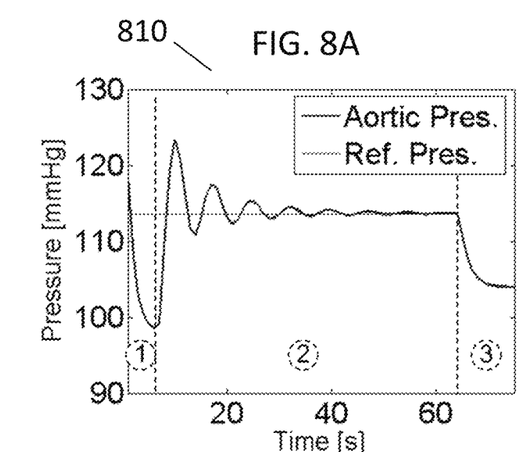
FIGS. 8A 8B, 8C, and 8D are a series of graphs illustrating coronary circulation parameters during an example simulation, according to an embodiment.
Figure 8B:
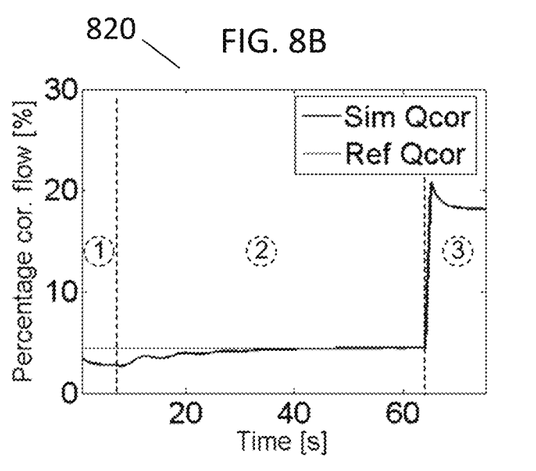
Figure 8C:
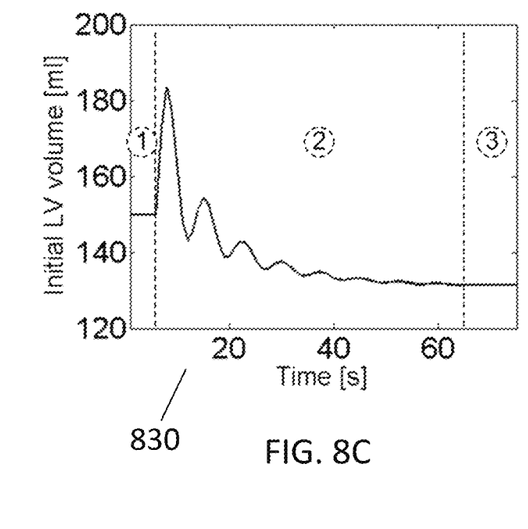
Figure 8D:
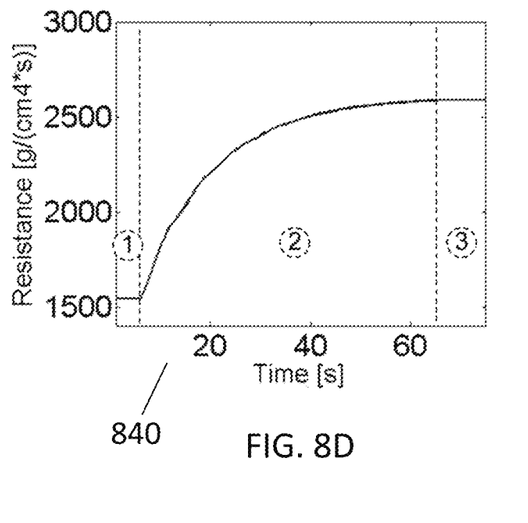

FIGS. 8A-8D display the evolution of the two controlled variables (aortic pressure (810 in FIG. 8A) and the percentage of coronary flow (820 in FIG. 8B)) and of the system inputs (systemic resistance (840 in FIG. 8D) and initial LV volume (830 in FIG. 8C)) during a simulation performed with the base values of the parameters. Each plot is divided into three sections: (1) represents the initialization period, (2) represents the period of time during which the feedback control system displayed in FIG. 4 is used and the rest state is simulated, and (3) represents the simulation of the hyperemic state. FIGS. 8A and 8B clearly show how, during phase (2) of the simulation, the values converge to the reference values estimated for the rest state of the patient. During phase (3) (hyperemia), the two system inputs remain constant (the feedback loops is no longer used), and, since the coronary resistance decreases, the aortic pressure decreases and the percentage coronary flow increases.

A method is introduced for estimating patient-specific coronary boundary conditions (at rest and hyperemia) together with a feedback control system which can be used to ensure that a CFD-based simulation matches the patient-specific coronary pressure and flow. The main advantages of this approach are that it is based solely on parameters, which are acquired non-invasively during the rest state, and that it can be used for full-order or reduced-order simulations. Further, it can be used to assess coronary diagnostic indexes which are based solely on the hyperemic state (e.g., FFR) or based on both rest and hyperemic state (e.g., CFR).

The proposed method does not take into consideration differences between genders (women require a higher resting flow for a similar amount of myocardial mass), but there is no study which also takes into account the gender when assessing resting coronary flow. Patients with rest angina have to be excluded, since angina means that rest flow does not match the oxygen demand, therefore equation (1) may no longer be valid. Hypertensive patients and patients with micro-vascular disease have to be modeled separately, since the TCRI values computed through equation (4) would be no longer valid.

The feedback control system 400 may be one or more processing devices, computing devices, processors, or the like for performing calculations and operations described herein. For example, one or more processors may be used to perform the calculations and operations of determining the rest state and hyperemic state boundary conditions, implementing the patient model 430 and the controllers 410 and 420, and determining the flow computations.

The feedback control system 400 may interface with one or more memory devices (not shown) such as read only memory (ROM), random access memory (RAM), and one or more optional non-transitory memory devices such as, for example, an external or internal DVD drive, a CD ROM drive, a hard drive, flash memory, a USB drive, or the like. The memory devices may be configured to include individual files and/or one or more databases for storing any software modules, instructions, or data.

Program instructions, software, or interactive modules for performing any of the functional steps associated with the processes as described above may be stored in the ROM and/or the RAM. Optionally, the program instructions may be stored on a tangible computer readable medium such as a compact disk, a digital disk, flash memory, a memory card, a USB drive, an optical disc storage medium, such as a Blu-Ray™ disc, and/or other recording medium.

An optional display interface may permit information from the feedback control system 400 to be displayed on one or more displays in audio, visual, graphic, and/or alphanumeric format. Communication with external devices may occur using various communication ports that may be attached to one or more communications networks, such as the Internet or a local area network, or directly to a portable computing device such as a notebook computer. An interface may allow for receipt of data from input devices such as a keyboard, a mouse, a joystick, a touch screen, a remote control, a pointing device, a video input device, an audio input device, and the like.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method of non-invasively determining coronary circulation parameters during a hyperemic state for a patient, the method comprising:
   obtaining an image of an anatomical framework of the patient through an image acquisition device;
   obtaining an anatomical model of a coronary tree of the patient based on the anatomical image;
   determining rest boundary conditions of the patient based on non-invasive measurements taken at a rest state, wherein the rest boundary conditions include a rate-pressure product, a flow through a particular vessel outlet, and terminal resistances;

computing hyperemic boundary conditions of the patient, wherein the hyperemic boundary conditions of the patient are a product of a total coronary resistance index and the rest boundary conditions of the patient;

adjusting the anatomical model to match the rest state by iteratively generating simulated values of flow and pressure until the simulated values match the rest boundary conditions, wherein parameters of the anatomical model are adjusted during each iteration using a plurality of controllers, each controller corresponding to a different output variable of the coronary tree; wherein a first controller of the plurality of controllers is a Proportional Integral (PI) controller that calculates coronary resistance of the coronary tree, and wherein a second controller of the plurality of controllers is a Proportional Integral Derivative (PID) controller that calculates a difference between an initial left ventricle volume and a dead volume;

adjusting the hyperemic boundary conditions based on the adjustments to the anatomical model;

performing a flow computation corresponding to the hyperemic state using the adjusted anatomical model; and providing a report identifying one or more results of the flow computation that includes a functional assessment of the patient's coronary tree and coronary flow reserve parameters.

2. The method of claim 1, wherein the anatomical model of the coronary tree of the patient is obtained via at least one of a CT scan, an MRI scan, an angiography scan, an ultrasound scan, and a cardiac perfusion scan.

3. The method of claim 1, wherein the non-invasive measurements taken at a rest state comprise one or more of heart rate, systolic blood pressure, and diastolic blood pressure.

4. The method of claim 1, wherein the rest boundary conditions of the patient comprise terminal resistance and capacitance values at vessel outlets during the rest state.

5. The method of claim 4, wherein the rest boundary conditions of the patient based on the terminal resistance and capacitance values at vessel outlets during the rest state are adjusted using information from a cardiac perfusion exam.

6. The method of claim 1, wherein the hyperemic boundary conditions of the patient based on the terminal resistance and capacitance values at vessel outlets during the hyperemic state are adjusted using information from a cardiac perfusion exam.

7. A feedback control system for non-invasively determining coronary circulation parameters during a hyperemic state for a patient, the system comprising:

one or more processors configured to calculate (i) rest boundary conditions of the patient based on non-invasive measurements taken at a rest state, wherein the rest boundary conditions include a rate-pressure product, a flow through a particular vessel outlet, and terminal resistances; and (ii) hyperemic boundary conditions of the patient, wherein the hyperemic boundary conditions of the patient are a product of a total coronary resistance index and the rest boundary conditions of the patient;

wherein the one or more processors are further configured to: adjust an anatomical model provided based on an anatomical image, to match the rest state by iteratively generating simulated values of flow and pressure until the simulated values match the rest boundary conditions, wherein parameters of the anatomical model are adjusted during each iteration using a plurality of controllers each controller corresponding to a different output variable of the coronary tree; wherein a first controller of the plurality of controllers is a Proportional Integral (PI) controller that calculates coronary resistance of the coronary tree, and wherein a second controller of the plurality of controllers is a Proportional Integral Derivative (PID) controller that calculates a difference between an initial left ventricle volume and a dead volume;

wherein the one or more processors are further configured to: adjust the hyperemic boundary conditions based on the adjustments to the parameters of the anatomical model; and perform a flow computation corresponding to the hyperemic state using the adjusted anatomical model;

wherein the one or more processors are further configured to: provide a report identifying one or more results of the flow computation that includes a functional assessment of the patient's coronary tree and coronary flow reserve parameters.

8. The system of claim 7, wherein the anatomical model of the coronary tree of the patient is obtained via at least one of a CT scan, an MM scan, an angiography scan, an ultrasound scan, and a cardiac perfusion scan.

9. The system of claim 7, wherein the non-invasive measurements taken at a rest state comprise one or more of heart rate, systolic blood pressure, and diastolic blood pressure.

10. The system of claim 7, wherein the rest boundary conditions of the patient comprise terminal resistance and capacitance values at vessel outlets during the rest state.

11. A non-transitory computer-readable media comprising software instructions for non-invasively determining coronary circulation parameters during a hyperemic state for a patient by:

obtaining an image of an anatomical framework of the patient through an image acquisition device;

obtaining an anatomical model of a coronary tree of the patient based on the anatomical image;

determining rest boundary conditions of the patient based on non-invasive measurements taken at a rest state, wherein the rest boundary conditions include a rate-pressure product, a flow through a particular vessel outlet, and terminal resistances;

computing hyperemic boundary conditions of the patient, wherein the hyperemic boundary conditions of the patient are a product of a total coronary resistance index and the rest boundary conditions of the patient;

adjusting the anatomical model to match the rest state by iteratively generating simulated values of flow and pressure until the simulated values match the rest boundary conditions, wherein parameters of the anatomical model are adjusted during each iteration using a plurality of controllers each controller corresponding to a different output variable of the coronary tree; wherein a first controller of the plurality of controllers is a Proportional Integral (PI) controller that calculates coronary resistance of the coronary tree, and wherein a second controller of the plurality of controllers is a Proportional Integral Derivative (PID) controller that calculates a difference between an initial left ventricle volume and a dead volume;

adjusting the hyperemic boundary conditions based on the adjustments to the anatomical model;

performing a flow computation corresponding to the hyperemic state using the adjusted anatomical model; and providing a report identifying one or more results of the flow computation that includes a functional assessment of the patient's coronary tree and coronary flow reserve parameters.

12. The non-transitory computer-readable media of claim 11, wherein the non-invasive measurements taken at a rest state comprise one or more of heart rate, systolic blood pressure, and diastolic blood pressure.

13. The non-transitory computer-readable media of claim 11, wherein the rest boundary conditions of the patient comprise terminal resistance and capacitance values at vessel outlets during the rest state.

* * * * *